United States Patent
Bae et al.

(10) Patent No.: US 12,358,082 B2
(45) Date of Patent: Jul. 15, 2025

(54) METHOD FOR INSPECTING WELDING QUALITY OF WELDED PORTION BETWEEN ELECTRODE TAB AND LEAD

(71) Applicant: LG ENERGY SOLUTION, LTD., Seoul (KR)

(72) Inventors: Sang Ho Bae, Daejeon (KR); Hun Bum Jung, Daejeon (KR); Jae Hwa Choi, Daejeon (KR); Ji Hun Hwang, Daejeon (KR); Cha Hun Ku, Daejeon (KR); Su Taek Jung, Daejeon (KR); Chang Min Han, Daejeon (KR); Young Seok Baek, Daejeon (KR)

(73) Assignee: LG ENERGY SOLUTION, LTD., Seoul (KR)

(*) Notice: Subject to any disclaimer, the term of this patent is extended or adjusted under 35 U.S.C. 154(b) by 214 days.

(21) Appl. No.: 17/801,107

(22) PCT Filed: Jun. 22, 2021

(86) PCT No.: PCT/KR2021/007801
§ 371 (c)(1),
(2) Date: Aug. 19, 2022

(87) PCT Pub. No.: WO2022/055085
PCT Pub. Date: Mar. 17, 2022

(65) Prior Publication Data
US 2023/0104232 A1    Apr. 6, 2023

(30) Foreign Application Priority Data
Sep. 10, 2020   (KR) .................. 10-2020-0116258

(51) Int. Cl.
*B23K 31/12*    (2006.01)
*B23K 101/38*   (2006.01)
(Continued)

(52) U.S. Cl.
CPC ............ *B23K 31/125* (2013.01); *G01B 11/02* (2013.01); *G01B 11/28* (2013.01); *G01N 33/207* (2019.01);
(Continued)

(58) Field of Classification Search
CPC .. B23K 31/125; B23K 2101/38; B23K 20/10; B23K 26/21; G01B 11/02; G01B 11/28;
(Continued)

(56) References Cited

U.S. PATENT DOCUMENTS

2012/0011934 A1   1/2012   Matsui et al.
2017/0182599 A1   6/2017   Tsukui
(Continued)

FOREIGN PATENT DOCUMENTS

CN    108132256 A    6/2018
CN    109187547 A    1/2019
(Continued)

OTHER PUBLICATIONS

International Search Report (with partial translation) and Written Opinion dated Sep. 8, 2021 issued in corresponding International Patent Application No. PCT/KR2021/007801.
(Continued)

*Primary Examiner* — Md M Rahman
(74) *Attorney, Agent, or Firm* — Morgan, Lewis & Bockius LLP

(57) ABSTRACT

The present invention relates to a method for inspecting a welding quality of an electrode tab-electrode lead welded portion of a pouch-type lithium secondary battery, and the method includes: recognizing welding traces of the welded portion by a vision inspection device; measuring a size of each of the recognized welding traces; and determining whether the welded portion has been weakly welded, exces-
(Continued)

sively welded or normally welded by comparing the measured size with a reference value.

9 Claims, 7 Drawing Sheets

(51) Int. Cl.
  *G01B 11/02* (2006.01)
  *G01B 11/28* (2006.01)
  *G01N 33/207* (2019.01)
  *H01M 50/536* (2021.01)
(52) U.S. Cl.
  CPC ....... *B23K 2101/38* (2018.08); *H01M 50/536* (2021.01)
(58) Field of Classification Search
  CPC .... G01B 5/0037; G01B 11/04; G01N 33/207; G01N 21/8851; G01N 21/95; G01N 2021/8854; G01N 2021/8887; H01M 50/536; G06T 2207/30152; G06T 7/0006; Y02E 60/10
  USPC ......................................................... 356/634
  See application file for complete search history.

(56) References Cited

U.S. PATENT DOCUMENTS

| | | | |
|---|---|---|---|
| 2019/0240788 A1 | 8/2019 | Park et al. | |
| 2020/0242753 A1 | 7/2020 | Shibata et al. | |

FOREIGN PATENT DOCUMENTS

| | | | |
|---|---|---|---|
| CN | 208986088 U | | 6/2019 |
| CN | 110023028 A | | 7/2019 |
| CN | 110686948 A | * | 1/2020 |
| DE | 19740024 C1 | | 3/1999 |
| JP | 2885040 B2 | | 4/1999 |
| JP | 2000-221016 A | | 8/2000 |
| JP | 2001-116522 A | | 4/2001 |
| JP | 3681928 B2 | | 8/2005 |
| JP | 2008-145252 A | | 6/2008 |
| JP | 2009-103691 A | | 5/2009 |
| JP | 4625892 B2 | | 2/2011 |
| JP | 4983236 B2 | | 7/2012 |
| JP | WO2010-113250 A1 | | 10/2012 |
| JP | 2013-165054 A | | 8/2013 |
| JP | 2014-024068 A | | 2/2014 |
| JP | 2015-205291 A | | 11/2015 |
| JP | 6369454 B2 | | 8/2018 |
| JP | 202322340 A | * | 1/2020 |
| JP | 2020-123459 A | | 8/2020 |
| JP | 6762163 B2 | | 9/2020 |
| KR | 10-2012-0096621 A | | 8/2012 |
| KR | 10-1305255 B1 | | 9/2013 |
| KR | 10-2015-0033268 A | | 4/2015 |
| KR | 10-2016-0059789 A | | 5/2016 |
| KR | 10-1678862 B1 | | 11/2016 |
| KR | 10-1736548 B1 | | 5/2017 |
| KR | 10-2105503 B1 | | 4/2020 |

OTHER PUBLICATIONS

Extended European Search Report dated Jul. 7, 2023 issued in the European Patent Application No. 21866956.2.
Office Action dated Sep. 4, 2023 issued in corresponding Japanese Patent Application No. 2022-549185.
Office Action dated Mar. 13, 2025, for the corresponding Chinese Patent Application No. 202180016005.1.

* cited by examiner

[FIG. 1]
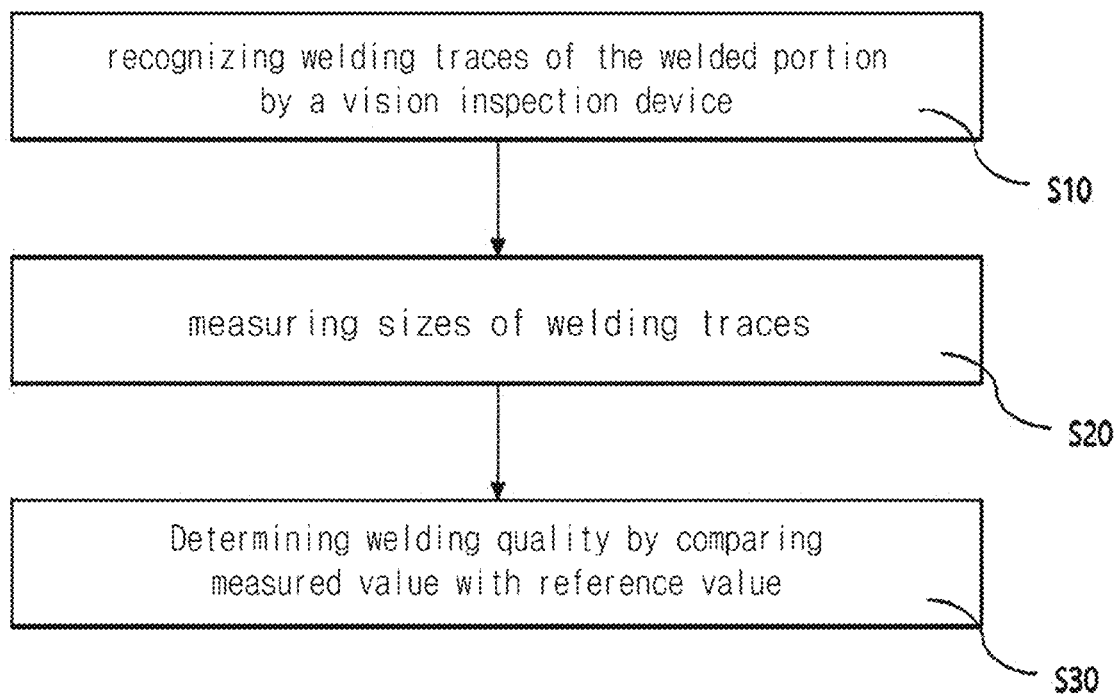

[FIG. 2]
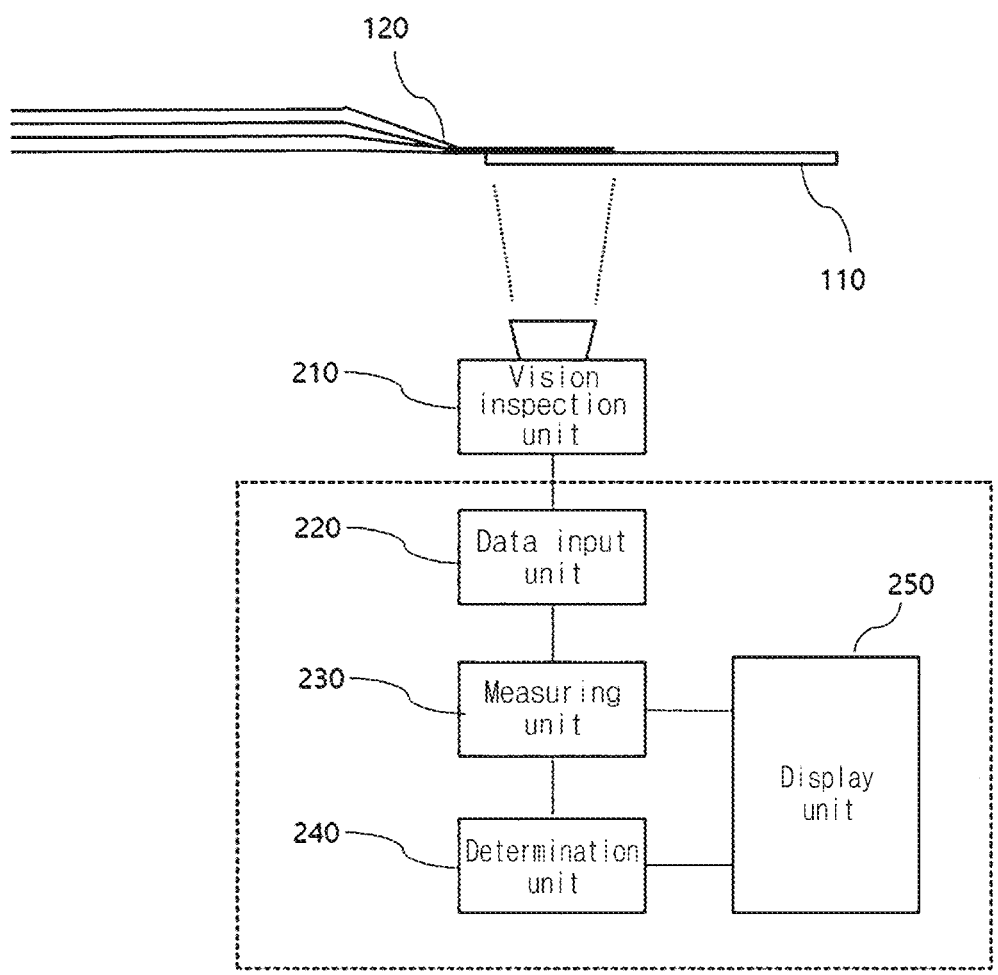

[FIG. 3]
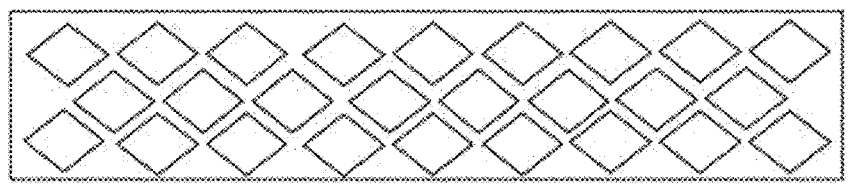
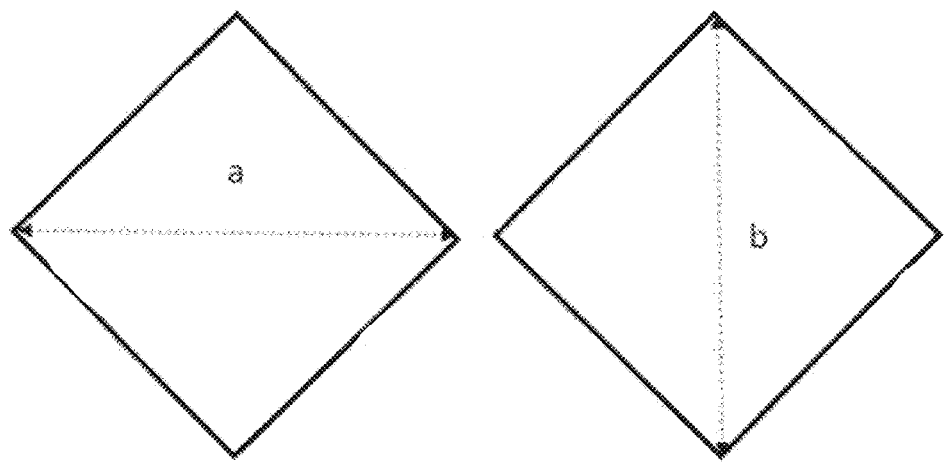

[FIG. 4]
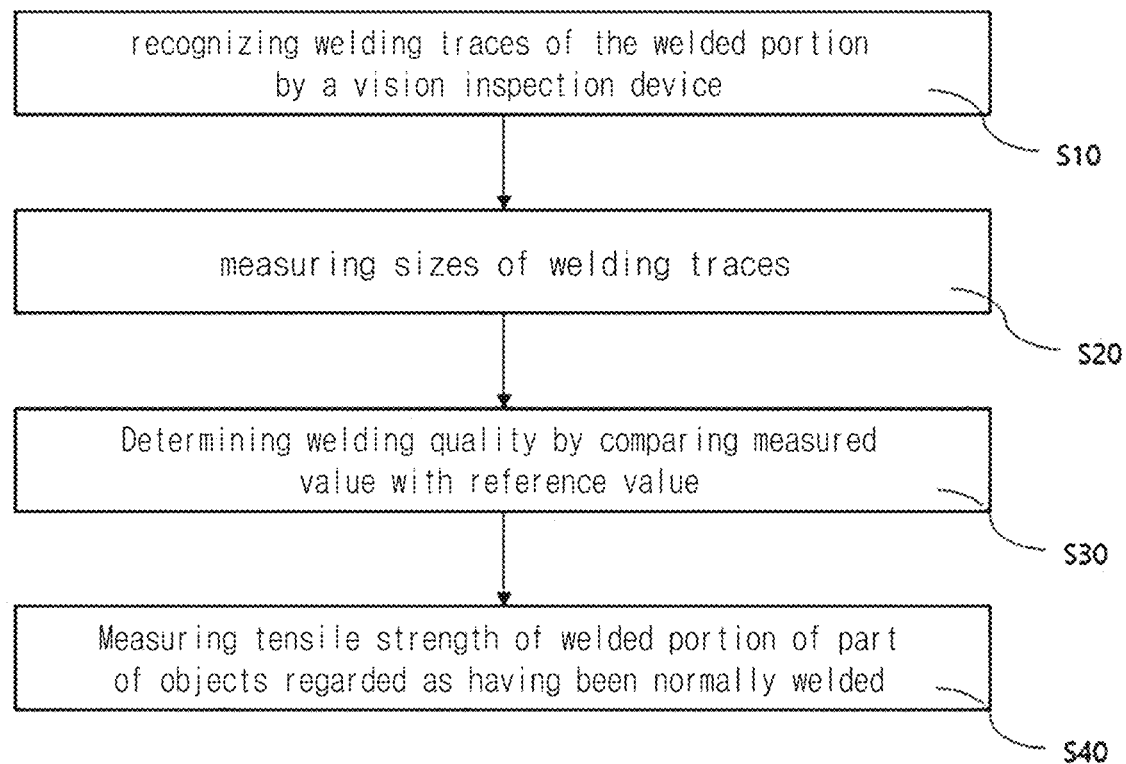

[FIG. 5]

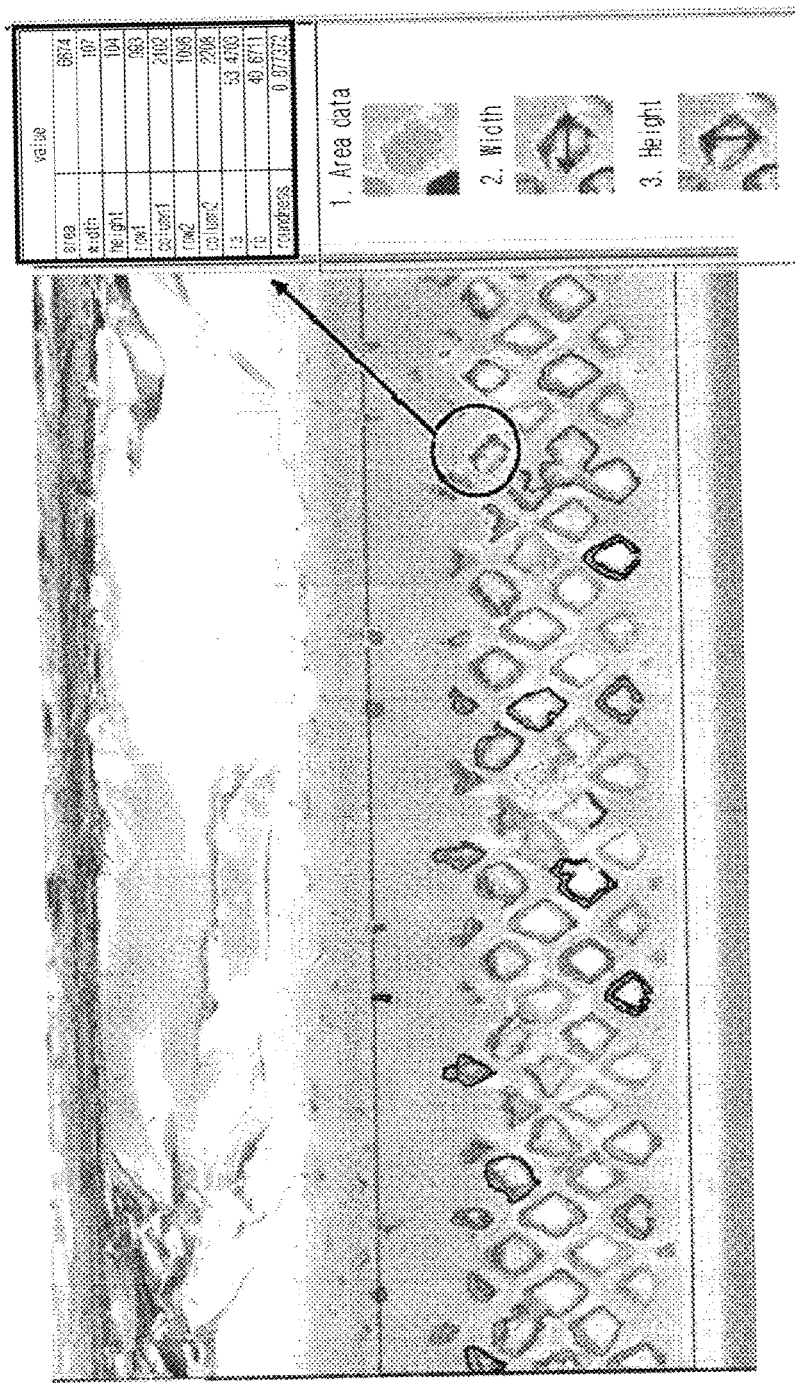
[FIG. 6]

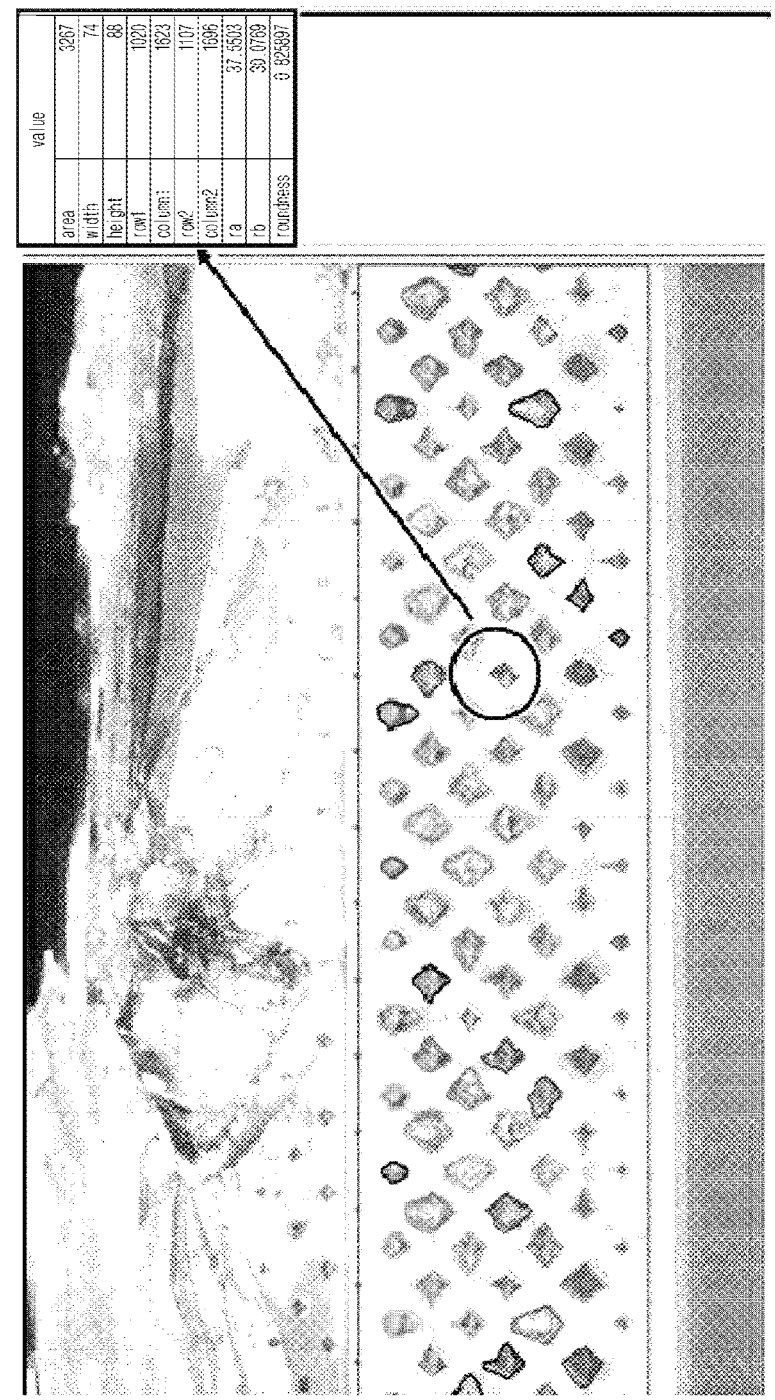
[FIG. 7]

METHOD FOR INSPECTING WELDING QUALITY OF WELDED PORTION BETWEEN ELECTRODE TAB AND LEAD

TECHNICAL FIELD

This application claims the benefit of priority based on Korean Patent Application No. 10-2020-0116258, filed on Sep. 10, 2020, and the entire contents of the Korean patent application are incorporated herein by reference.

The present invention relates to a method of inspecting a welding quality for determining a welded portion of an electrode tab and an electrode lead has been weakly welded, excessively welded or normally welded.

BACKGROUND ART

As technologies for mobile devices are developed and demand for the mobile devices increases, there has been a rapid increase in demand for secondary batteries as energy sources. Among such secondary batteries, lithium secondary batteries, which exhibit a high energy density and operational potential, a long cycle life, and a low self-discharge rate have been commercialized and widely used.

The lithium secondary battery has a structure where a non-aqueous electrolyte containing a lithium salt is impregnated in an electrode assembly in which a porous separator is interposed between a positive electrode and a negative electrode where an active material has been applied on a current collector.

Such a lithium secondary battery may be classified into a can-type secondary battery in which the cell assembly is embedded in a metal can, and a pouch-type secondary battery in which the cell assembly is embedded in a pouch case of an aluminum laminate sheet, depending on the shape of the exterior material case.

Pouch-type lithium secondary batteries are drawing attention as the power source of electric vehicles or hybrid vehicles due to a low price, a high energy density, and advantage that it is easy to form a large capacity battery pack through serial or parallel connection. Such a pouch-type lithium secondary battery has a structure in which a cell assembly, to which a plate-type electrode lead is connected, is sealed together with an electrolyte solution in a pouch case. A part of the electrode lead is exposed to the outside of the pouch case, and the exposed electrode lead is electrically connected to a device where a secondary battery is mounted or is used to electrically connect secondary batteries.

The pouch-type lithium secondary battery includes an electrode assembly, a plurality of electrode tabs extending from the electrode assembly, electrode leads welded to the electrode tabs, and a pouch-type exterior material accommodating the electrode assembly.

Such electrode tabs are extended from each electrode plate of the electrode assembly, the electrode leads are electrically connected to the plurality of electrode tabs extended from respective electrode plates and are coupled in a form that is partly exposed to the outside of the pouch case.

When the electrode tab and the electrode lead are welded, laser welding, resistance welding and ultrasonic welding may be used. Herein, the ultrasonic welding is a scheme which generates ultrasonic vibrations of 10 to 75 kHz and welds metal through ultrasonic vibration friction heat between metals. Namely, if ultrasonic vibration is applied by the ultrasonic welding device in a state that the electrode tab contacts the electrode lead, friction heat is generated on the contact surface between the electrode tab and the electrode lead, and the electrode tab and the electrode lead are welded by the generated friction heat.

The welding quality of the electrode tab-electrode lead welded portion was checked by measuring the tensile strength by pulling the electrode tab and the electrode lead by a gripper, respectively, but since this is a destructive inspection method, total inspection is impossible, and the welding quality can be checked by only an intermittent sample test.

Korean Patent No. 10-1678662 discloses a technology for determining the welding quality by measuring welding points of an inspection area by vision and comparing the sum of the welding points with the welding strength. However, since the inspection area is limited to some pressure points in the above-described technology, reliability decreases. Hence, there is a need for development of a technology about a non-destructive inspection method capable of improving reliability of inspection in inspecting the welding quality of the electrode tab-electrode lead welded portion.

DISCLOSURE

Technical Problem

The present invention has been made to solve the above problems, and an object of the present invention is to provide a method of inspecting a welding quality of an electrode tab-electrode lead welded portion of a pouch-type lithium secondary battery in a non-destructive manner.

Further, an object of the present invention is to provide an inspection method capable of determining the welding quality in a simplified method.

Technical Solution

A method of inspecting a welding quality according to an embodiment of the present invention includes: recognizing welding traces of the welded portion by a vision inspection device; measuring a size of each of the recognized welding traces; and determining whether the welded portion has been weakly welded, excessively welded or normally welded by comparing the measured size with a reference value.

In an embodiment of the present invention, the measuring includes measuring a diagonal length of each of the welding traces.

In an embodiment of the present invention, the welded portion may be welded by an ultrasonic welding or laser welding method.

In an embodiment of the present invention, the recognizing may include vision-inspecting an electrode lead surface of the welded portion.

In an embodiment of the present invention, the measuring may include measuring an area of each of the welding traces.

In an embodiment of the present invention, the reference value may be obtained from welding quality correlation data according to a pitch of a welding horn.

In an embodiment of the present invention, the determining may include determining that the welded portion has been weakly welded if an average value of sizes of the welding traces is smaller than the reference value and determining that the welded portion has been excessively welded if the average value is greater than the reference value.

In an embodiment of the present invention, the measuring may include measuring sizes remaining pressure points except for pressure points existing on a first line of each of an upper side, a lower side, a left side and a right side of the welded portion.

In an embodiment of the present invention, the method includes inspecting a tensile strength of an object determined as having been normally welded during the determining.

Advantageous Effects

According to the present invention, since a welding quality is measured by comparing the measurement value of the length of the diagonal line of the welding trace of the welded portion with the reference value, the welding quality can be measured in a simple method.

According to the present invention, since the lead surface of the welded portion is vision-inspected, the boundary of the welded portion can be clearly recognized, and the welding quality inspection can be more accurately performed.

BRIEF DESCRIPTION OF THE DRAWINGS

FIG. 1 is a flowchart illustrating the order of a method of inspecting a welding quality according to an embodiment of the present invention.

FIG. 2 is a schematic diagram showing a vision inspection process according to an embodiment of the present invention.

FIG. 3 is a conceptual diagram showing sizes of welding traces.

FIG. 4 is a flowchart illustrating the order of a method of inspecting a welding quality according to another embodiment of the present invention.

FIGS. 5 to 7 are diagrams showing the results of vision-measuring sizes of welding traces according to an embodiment of the present invention.

DETAILED DESCRIPTION OF THE PREFERRED EMBODIMENTS

Hereinafter, the present invention will be described in detail with reference to the drawings. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

In this application, it should be understood that terms such as "include" or "have" are intended to indicate that there is a feature, number, step, operation, component, part, or a combination thereof described on the specification, and they do not exclude in advance the possibility of the presence or addition of one or more other features or numbers, steps, operations, components, parts or combinations thereof. Also, when a portion such as a layer, a film, an area, a plate, etc. is referred to as being "on" another portion, this includes not only the case where the portion is "directly on" the another portion but also the case where further another portion is interposed therebetween. On the other hand, when a portion such as a layer, a film, an area, a plate, etc. is referred to as being "under" another portion, this includes not only the case where the portion is "directly under" the another portion but also the case where further another portion is interposed therebetween. In addition, to be disposed "on" in the present application may include the case disposed at the bottom as well as the top.

Hereinafter, the present invention will be described in detail with reference to the drawings.

FIG. 1 is a flowchart illustrating the order of a method of inspecting a welding quality according to an embodiment of the present invention. Referring to FIG. 1, a method of inspecting a welding quality of the present invention is a method for inspecting a welding quality of an electrode tab-electrode lead welded portion of a pouch-type lithium secondary battery, and the method includes: recognizing welding traces of the welded portion by a vision inspection device (S10); measuring a size of each of the recognized welding traces (S20); and determining whether the welded portion has been weakly welded, excessively welded or normally welded by comparing the measured size with a reference value (S30).

The inventors of the present invention have devised the present invention of measuring the welding quality by measuring the size of the welding trace of the welded portion in view of the fact that the larger the welding strength of the welded portion, the larger the welding trace.

The welding trace in the present invention is a concept including welding pressure points in the case of an ultrasonic welding method and welding beads in the case of a laser welding method.

In the conventional welding quality inspection method, only the tensile strength was measured by pulling the electrode tab and the electrode lead by a gripper, respectively. However, since the battery is broken in this method, only intermittent inspection like a sample test was performed. However, according to the welding quality inspection method of the present invention, welding traces of the welded portion are vision-inspected, and the sizes of the welding traces recognized in the vision inspection are measured to thereby determine the welding quality. In this case, since the battery is not broken at the time of the welding quality inspection, all batteries can be inspected.

The vision inspection step (S10) includes recognizing welding traces of the welded portion, where the electrode tab and the electrode lead have been welded, by a vision inspection device. The vision inspection device may be a microscope or an imaging camera.

FIG. 2 is a schematic diagram showing a vision inspection process for an ultrasonic welding portion according to an embodiment of the present invention. Referring to FIG. 2, a vision inspection unit 210 may photograph or scan the welded portion and transmit image data or image files to a data input unit 220. The data input unit 220 may transmit data such as images, which are received from the vision inspection unit 210, to a measuring unit 230, and the measuring unit 230 may measure lengths of diagonal lines of pressure points from images, which are received form the data input unit 220, and/or areas of the pressure points, and transmit the measurement result information to a data storage unit (not shown), a display unit 250, or a determination unit 240. Further, the determination unit 240 compares the lengths of diagonal lines of pressure points, which represent the sizes of the pressure points received from the measuring unit 230, and/or the areas of the pressure points, with the reference value, which becomes the basis for determining whether there is a welding defect, to thereby determine whether the welded portion has been weakly welded, excessively welded or normally welded.

Referring to FIG. 2, in the case of ultrasonic welding, welding is performed in a state that an electrode tab 120 is positioned on the upper portion of an electrode lead, and the vision inspection unit 210 vision-inspect the back surface, which is the electrode lead surface, among the top surface and the back surface of the welded portion of the electrode tab 100 and the electrode lead 110. This is because the upper surface of the welded portion is an electrode tab surface, and the electrode tab is made of an electrode current collector foil, and thus the boundary of the welding trace is not clearly recognized at the time of vision inspection due to light reflex. On the contrary, the lead surface, which is the lower surface of the welded portion, does not have a problem that the boundary becomes unclear due to light reflex. As such, the inspection method of the present invention is characterized in performing vision inspection for the lead surface of the welded portion in the vision inspection step.

Further, in the case of the laser welding, the welding is performed in a state that the electrode tab is located under the electrode lead unlike the ultrasonic welding. As such, in this case, the vision inspection unit vision-inspects the upper surface which is the electrode lead surface of the electrode lead welded portion.

In the measuring step (S20), the sizes of the welding traces are measured from the image of the welded portion obtained by the vision inspection. In one specific example, the size of the pressure point may be the length of the diagonal line of the welding trace. FIG. 3 is a conceptual diagram showing sizes of welding traces. Referring to FIG. 3, the welded portion includes a plurality of welding traces, and one welding trace has a form of rhombus. The size of the welding trace in a rhombus shape may be estimated by the length of the diagonal line (a, b) which is the distance between two vertexes facing each other.

In one specific example, the size of the welding trace may be estimated by measuring the area of the welding trace. There may be various methods of measuring the area of the welding trace, but in one preferred example, a method of measuring an image in pixel units may be used. By recognizing the number of pixels corresponding to the area occupied by the welding trace in the image, automation is possible, and uniform measurement criteria may be applied.

In one specific example, the measuring step may be to measure the sizes of remaining pressure points except for pressure points existing on each first line of an upper side, a lower side, a left side and a right side of the welded portion in the image obtained at the vision inspection step.

FIGS. 6 and 7 illustrate an image of a welded portion obtained from a vision inspection unit according to an embodiment of the present invention. FIG. 6 shows an image of a lead surface in a welded portion of a positive electrode tab and a lead, and FIG. 7 shows an image of a lead surface in a welded portion of a negative electrode tab and a lead. The measuring unit may measure the area and the length of the diagonal line (width, height) for a plurality of welding traces from the image and display their measurement values. Further, the sizes of all welding traces in the inspection area may be measured, but pressure points existing on each first line of an upper side, a lower side, a left side and a right side are not measured. Referring to FIG. 6, sizes of pressure points existing on the first line of the upper portion are significantly smaller than sizes of other pressure points. Referring to FIG. 7, the sizes of pressure points existing on the first line of the inspection area are significantly smaller than sizes of other pressure points. Hence, since these welding traces become a noise, they are excluded at the time of the welding quality inspection.

The determining step (S30) is a step of determining whether there is a welding defect in the welded portion by comparing the area and the length of the diagonal line of the welding trace measured in the measuring step (S20) with the reference value. The determining step includes a process of setting a numerical value range of the sizes of welding traces, which satisfy normal welding requirements, to a reference value, based on welding quality result data according to sizes of welding traces in advance, and determining that the welded portion has been weakly welded if the numerical range is below the preset reference value, determining that the welded portion has been excessively welded if the numerical range is above the reference value, and determining that the welded portion has been normally welded if the numerical range corresponds to the reference value.

In one specific example, the reference value may be obtained from welding quality correlation data according to a pitch of a welding horn. Herein, the welding horn refers to a member included in an ultrasonic welding device. The ultrasonic welding is to join objects by ultrasonic vibrations in a state that a welded object is inserted between horn and anvil welding bodies. At this time, the welding conditions may be determined by adjusting the pitch of the horn. In one preferred example, the reference value may be set based on the horn pitch.

The length of the horn pitch is the length of one side in the welding trace of a rhombus form, and when assuming that the lengths of 4 sides are the same, the length of the diagonal line is 1.27 mm (=0.9*$\sqrt{2}$) when the pitch of the horn is 0.9 mm. Namely, based on 1.27 mm, which is the length of the diagonal line of the welding horn having the pitch of 0.9 mm, the numerical range (=0.889 mm to 1.016 mm) corresponding to 70 to 80% of the length may be set to the reference value.

FIG. 5 shows the result of setting a reference value according to the pitch of a horn and determining the welding quality according to the set reference value, according to an embodiment of the present invention. When the horn pitch is 0.9 mm, the reference value of the normal welding is in the range of 0.889 to 1.016 mm. Hence, when the size of the welding trace is below the above numerical value range, it is determined as a weak welding, and when the size is above the above numerical value range, it is determined as an excessive welding. Even when the horn pitch is 1.2 mm, it is possible to determine whether the welding corresponds to a weak welding, an excessive welding or a normal welding, by setting a reference value.

The method of determining the welding quality by comparing lengths of diagonal lines of welding traces is simpler than the method of determining the welding quality by comparing welded areas.

FIG. 5 shows an example of determining whether there is a welding defect by measuring lengths of diagonal lines of welding traces, but it is also possible to determine whether there is a welding defect by measuring areas occupied by the welding traces.

Further, there are a plurality of welding traces, and the areas and lengths of respective diagonal lines of the welding traces are different. Hence, the welding quality can be determined by measuring the areas and lengths of respective diagonal lines of the welding traces, calculating the average value of the measured values, and comparing the average value with the reference value.

FIG. 4 is a flowchart illustrating the order of a method of inspecting a welding quality according to another embodiment of the present invention. Referring to FIG. 4, it is possible to include a process of additionally performing a tensile strength inspection for an object, which is determined as having been normally welded, after performing the above-described non-destructive welding quality inspection method. In the case of the method of determining the welding quality by vision-measuring the size of the welding trace, the welding strength is estimated form the size of the welding trace, and thus the welding may be regarded as a normal welding even when it actually is a weak welding. As such, a tensile strength inspection is additionally performed. Since the tensile strength inspection is a destructive inspection in which the welded portion is broken, it is not possible to perform inspection for all objects which are determined as being normal, and the inspection is intermittently performed for a few objects. Since the inspection method of the present invention includes the above-described non-destructive inspection for all battery cells, it can supplement intermittent tensile strength inspection.

Further, the battery, which is inspected by the inspection method of the present invention, may have a structure in which an electrode assembly having a structure, where a positive electrode, a separator, and a negative electrode are alternately stacked, is accommodated in a battery case. The positive electrode and the negative electrode each have a structure where an electrode slurry containing an electrode active material is applied on a current collector, which was then dried and rolled to thereby form an active material layer. When an electrode assembly is accommodated in a battery case, an electrolyte solution may be injected into the inside and be sealed to thereby manufacture a battery cell.

Herein, the current collector may be a positive electrode current collector or a negative electrode current collector, and the electrode active material may be a positive electrode active material or a negative electrode active material. In addition, the electrode slurry may further include a conductive material and a binder in addition to the electrode active material.

In the present invention, the positive electrode collector generally has a thickness of 3 to 500 micrometers. The positive electrode current collector is not particularly limited as long as it has high conductivity without causing a chemical change in the battery. Examples of the positive electrode current collector include stainless steel, aluminum, nickel, titanium, sintered carbon or aluminum or stainless steel of which the surface has been treated with carbon, nickel, titanium, silver, or the like. The current collector may have fine irregularities on the surface thereof to increase the adhesion of the positive electrode active material, and various forms such as a film, a sheet, a foil, a net, a porous body, a foam, and a nonwoven fabric are possible.

The sheet for the negative electrode collector generally has a thickness of 3 to 500 micrometers. The negative electrode current collector is not particularly limited as long as it has electrical conductivity without causing chemical changes in the battery, and examples thereof include copper, stainless steel, aluminum, nickel, titanium, sintered carbon, copper or stainless steel of which the surface has been treated with carbon, nickel, titanium, silver or the like, aluminum-cadmium alloy, or the like. In addition, like the positive electrode current collector, fine unevenness can be formed on the surface to enhance the bonding force of the negative electrode active material, and it can be used in various forms such as a film, a sheet, a foil, a net, a porous body, a foam, and a nonwoven fabric.

In the present invention, the positive electrode active material is a material capable of causing an electrochemical reaction and a lithium transition metal oxide, and contains two or more transition metals. Examples thereof include: layered compounds such as lithium cobalt oxide ($LiCoO_2$) and lithium nickel oxide ($LiNiO_2$) substituted with one or more transition metals; lithium manganese oxide substituted with one or more transition metals; lithium nickel oxide represented by the formula $LiNi_{1-y}M_yO_2$ (wherein M=Co, Mn, Al, Cu, Fe, Mg, B, Cr, Zn or Ga and contains at least one of the above elements, $0.01 \leq y \leq 0.7$); lithium nickel cobalt manganese composite oxide represented by the formula $Li_{1+z}Ni_bMn_cCo_{1-(b+c+d)}M_dO_{(2-e)}A_e$ such as $Li_{1+z}Ni_{1/3}Co_{1/3}Mn_{1/3}O_2$, $Li_{1+z}Ni_{0.4}Mn_{0.4}Co_{0.2}O_2$ etc. (wherein $-0.5 \leq z \leq 0.5$, $0.1 \leq b \leq 0.8$, $0.1 \leq c \leq 0.8$, $0 \leq d \leq 0.2$, $0 \leq e \leq 0.2$, $b+c+d<1$, M=Al, Mg, Cr, Ti, Si or Y, and A=F, P or CO; olivine-based lithium metal phosphate represented by the formula $Li_{1+x}M_{1-y}M'_yPO_{4-z}X_z$ (wherein M=transition metal, preferably Fe, Mn, Co or Ni, M'=Al, Mg or Ti, X=F, S or N, and $-0.5 \leq x \leq 0.5$, $0 \leq y \leq 0.5$, $0 \leq z \leq 0.1$).

Examples of the negative electrode active material include carbon such as non-graphitized carbon and graphite carbon; metal complex oxide such as $Li_xFe_2O_3$ ($0 \leq x \leq 1$), $Li_xWO_2$ ($0 \leq x \leq 1$), $Sn_xMe_{1-x}Me'_yO_z$ (Me: Mn, Fe, Pb, Ge; Me': Al, B, P, Si, groups 1, 2, and 3 of the periodic table, halogen; $0<x \leq 1$; $1 \leq y \leq 3$; $1 \leq z \leq 8$); lithium metal; lithium alloy; silicon alloy; tin alloy; metal oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, and $Bi_2O_5$; conductive polymers such as polyacetylene; and Li—Co—Ni-based materials.

The conductive material is usually added in an amount of 1 to 30% by weight based on the total weight of the mixture including the positive electrode active material. Such a conductive material is not particularly limited as long as it has electrical conductivity without causing a chemical change in the battery, and examples thereof include graphite such as natural graphite and artificial graphite; carbon black such as carbon black, acetylene black, Ketjen black, channel black, furnace black, lamp black, and summer black; conductive fibers such as carbon fiber and metal fiber; metal powders such as carbon fluoride, aluminum and nickel powder; conductive whiskey such as zinc oxide and potassium titanate; conductive metal oxides such as titanium oxide; and conductive materials such as polyphenylene derivatives and the like.

The binder is added in an amount of 1 to 30% by weight, on the basis of the total weight of the mixture containing the positive electrode active material, as a component that assists in bonding between the active material and the conductive material and bonding to the current collector. Examples of such binders include polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, ethylene-propylene-diene terpolymer (EPDM), sulfonated EPDM, styrene butylene rubber, fluorine rubber, various copolymers and the like.

Further, the separator is interposed between the positive electrode and the negative electrode, and an insulating thin film having high ion permeability and mechanical strength is used. The pore diameter of the separator is generally 0.01 to 10 micrometers, and the thickness is generally 5 to 300 micrometers. Examples of such a separator include olefin-based polymers such as polypropylene which is chemically resistant and hydrophobic; a sheet or a nonwoven fabric made of glass fiber, polyethylene or the like.

In an electrode assembly, an electrode tab is formed at one side of an electrode, and the electrode tab may be a positive electrode tab or a negative electrode tab. A positive electrode lead and a negative electrode lead are connected to the positive electrode tab and the negative electrode tab, respectively. The positive electrode lead and the negative electrode lead are drawn to the outside to thereby play a role of a terminal which is electrically connected to the outside. At this time, the positive electrode lead and the negative electrode lead may be joined to the positive electrode tab and the negative electrode tab, respectively, by welding.

Further, the battery case is not particularly limited as long as it is used as an exterior material for packaging the battery, and a cylindrical, square, or pouch type may be used and specifically a pouch-type battery case may be used. The pouch-type battery case is generally made of an aluminum laminate sheet and may be composed of an inner sealant layer for sealing, a metal layer for preventing permeation of materials, and an external resin layer forming the outermost part of the case. Details of the battery case are known to those of ordinary skill in the art, and thus detailed description thereof will be omitted.

In the electrode constituting the electrode assembly, an electrode tab is drawn out to one side for electric connection with an external device or another battery cell. The electrode tab may be a positive electrode tab or a negative electrode tab, and the positive electrode tab and the negative electrode tab may be coupled by the welding with the electrode lead. The electrode lead is drawn to the outside of the battery case.

On the other hand, in this specification, terms indicating directions such as up, down, left, right, before, and after are used, but it is obvious that these terms are for convenience of description only and may change depending on the location of the object or the location of the observer.

DESCRIPTION OF REFERENCE NUMERALS

110: electrode lead
120: electrode tab
a, b: diagonal length of welding trace

The invention claimed is:

1. A method for inspecting a welding quality of an electrode tab-electrode lead welded portion of a pouch-type lithium secondary battery, comprising: obtaining the electrode tab-electrode lead welded portion welded by an ultrasonic welding device having a predetermined horn pitch, detecting welding traces of the welded portion by a vision inspection device; measuring a size of each of the recognized welding traces; and determining whether the welded portion has been weakly welded, excessively welded or normally welded by comparing the measured size with a reference value, wherein the reference value is determined based on the predetermined horn pitch;

wherein the determining includes determining that the welded portion has been weakly welded when an average value of sizes of the welding traces is smaller than the reference value, and determining that the welded portion has been excessively welded when the average value is greater than the reference value.

2. The method of claim 1, wherein the measuring includes measuring a diagonal length of each of the welding traces.

3. The method of claim 2, wherein the measuring includes measuring an area of each of the welding traces.

4. The method of claim 1, wherein the welded portion is welded by an ultrasonic welding.

5. The method of claim 4, wherein the reference value is obtained from welding quality correlation data according to a pitch of a welding horn.

6. The method of claim 1, wherein the detecting includes vision-inspecting an electrode lead surface of the welded portion.

7. The method of claim 1, wherein the measuring includes measuring sizes remaining pressure points except for pressure points existing on a first line of each of an upper side, a lower side, a left side and a right side of the welded portion.

8. The method of claim 1, further comprising inspecting a tensile strength of an object determined as having been normally welded during the determining.

9. The method of claim 1, wherein the determining includes comparing lengths of diagonal lines of pressure points.

* * * * *